United States Patent [19]

Puderbaugh et al.

[11] 4,185,072
[45] Jan. 22, 1980

[54] ORTHOPEDIC CEMENT MIXER

[75] Inventors: George Puderbaugh, Manlius; Robert W. Pike, Syracuse; Thomas S. Myers, Sherrill; James H. Frakes, Jr., Manlius, all of N.Y.

[73] Assignee: Diemolding Corporation, Canastota, N.Y.

[21] Appl. No.: 769,552

[22] Filed: Feb. 17, 1977

[51] Int. Cl.² ............................ B01L 1/00; B01F 7/16
[52] U.S. Cl. ..................................... 422/99; 366/139; 366/248; 422/104; 422/225
[58] Field of Search ............. 23/292, 259 (U.S. only); 259/108, 122, DIG. 20; 128/DIG. 28; 98/115 R; 366/139, 248; 422/99, 104, 225

[56] References Cited

U.S. PATENT DOCUMENTS

| | | | |
|---|---|---|---|
| 1,794,874 | 3/1931 | Trescott | 23/259 X |
| 2,777,177 | 1/1957 | Steinbock, Jr. et al. | 259/108 UX |
| 2,958,517 | 11/1960 | Harker et al. | 259/108 X |
| 3,738,619 | 6/1973 | Shirae | 259/108 |
| 4,015,945 | 4/1977 | Frankel et al. | 23/292 |

Primary Examiner—Joseph Scovronek
Attorney, Agent, or Firm—James Magee, Jr.

[57] ABSTRACT

The specification discloses a combination mixing-reaction apparatus comprising a mixing vessel within an evacuable housing, mixing vanes operable from outside of the apparatus. The housing is provided with vacuum conduits which can be connected to a vacuum source for withdrawing vapors and gaseous reaction products from within the apparatus.

3 Claims, 12 Drawing Figures

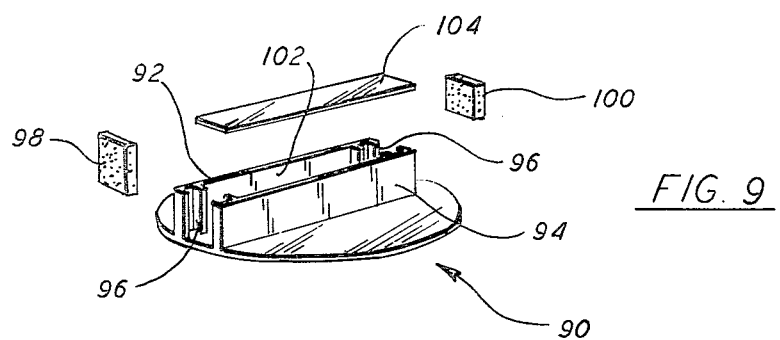
FIG. 9
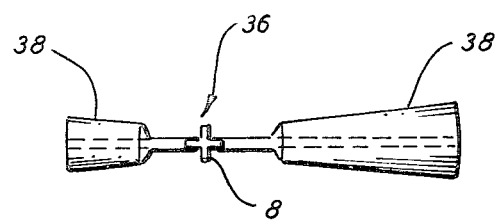
FIG. 12
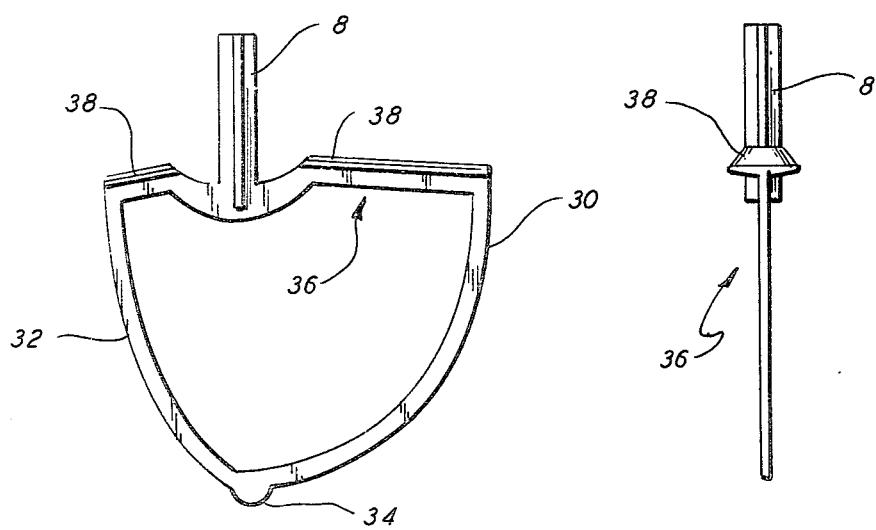
FIG. 10
FIG. 11

ORTHOPEDIC CEMENT MIXER

BACKGROUND OF THE INVENTION

This invention relates to an apparatus for compounding a polymeric reaction product, and more particularly to a combination reaction-mixing vessel for the preparation of acrylic polymers.

In many orthopedic surgical procedures it is necessary to employ a bonding material to set implants such as pins and artificial joints in bone. The cement which is employed for this purpose is generally a polymeric material which is prepared by copolymerization of its components as needed. Because of the necessity for a fairly quick setting material the cement is almost universally prepared by a surgical assistant during the course of the operation right in the sterile field of the operating room. The preparation of the cement involves admixture of the cement components in a suitable reaction vessel to form a uniform polymeric reaction product. The cement is usually an acrylic material, comprising a reaction product of methylmethacrylate monomer and polymethylmethacrylate-methylmethacrylate-styrene copolymer. In order to provide a cement which has the desired properties and which has the desired fixation of the implants it is necessary that the compounds be uniformly and thoroughly admixed so that a homogeneous reaction product is produced. During mixing and the consequent reaction there are produced various vapors which may comprise a gaseous form of a volatile component or a gaseous reaction product. Because of the noxious and toxic nature of such vapors it is highly undesirable to be exposed to them, particularly for extended periods of time in the course of multiple preparations. Since it is necessary that mixing be carried out for a period of up to four or five minutes in order to insure a uniform reaction product and a minimum concentration of volatile reactants, the period of exposure to harmful vapors can be substantial.

It is an object of this invention to provide an apparatus for mixing acrylic bone cement which is capable of producing a uniform admixture of reactants.

Another object of the invention is to provide an apparatus which provides safe and effective operation in the preparation of acrylic polymers.

A further object of the invention is to provide a mixing device from which fumes and gaseous reaction products can be removed and conveyed to a remote location for disposal.

Another object of the invention is to provide a safe and easily operable mixing-reaction vessel which is disposable after use.

A still further object of the invention is to provide for consistent mechanical mixing of acrylic cement reactants without exposure of the operator to toxic or noxious by-products.

BRIEF DESCRIPTION OF THE INVENTION

These and other related objects can be achieved by a device which comprises a reaction-mixing vessel which can be charged with pre-measured amounts of reactants, through a suitable orifice which can then be closed during the mixing operation. Such a device comprises an open vessel to contain the reactants, a cover or top for such vessel, mixing means associated with said cover operable from the exterior of the covered vessel, and vacuum conduit means communicating between the interior of the vessel and a remote vacuum source.

FIG. 9 is a perspective view of a vessel base.

FIGS. 10, 11, and 12 are various views of another embodiment of the mixing vanes having a plow-member on the top of the vane.

Figure 2:
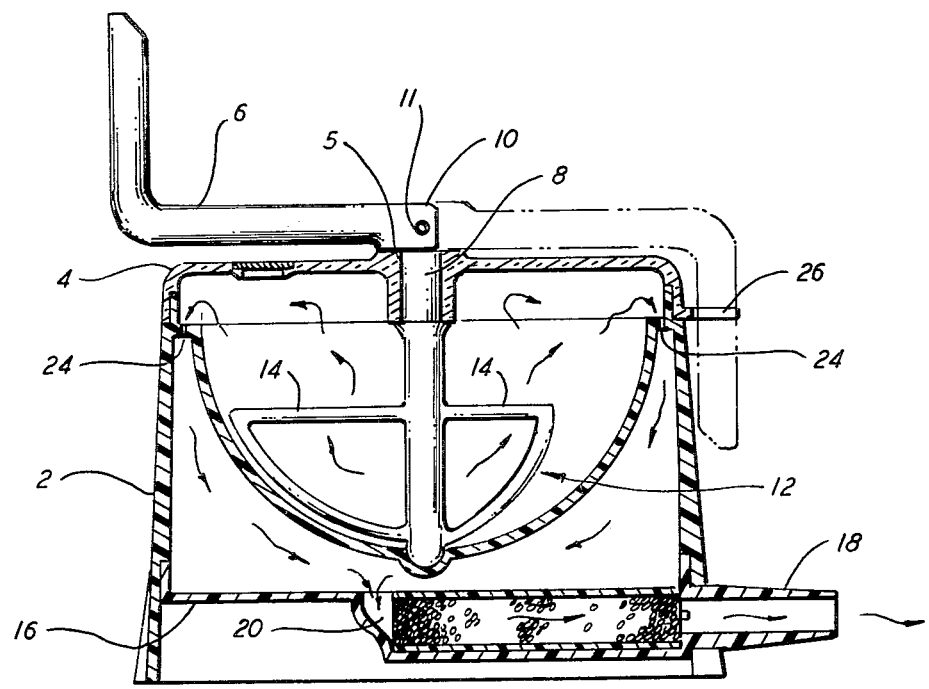
FIG. 2 is a sectional view of the device of FIG. 1.

In FIG. 2 the operative internal parts of the mixing apparatus are shown. Handle 6 is position to be grasped and rotated by the operator. The handle 6 is connected to the shaft 8 by pin 11. Shaft 8 extends through cover 4 downwardly into the reaction-mixing chamber so that mixing vanes 14 can be rotated. The housing is provided with vents 24 and vacuum exhaust port 18 which communicates through the housing and filter unit 20 with vents 24. The vents can be more clearly seen in FIG. 3. The filter is placed in a well which forms part of Floor 16.

Figure 3:
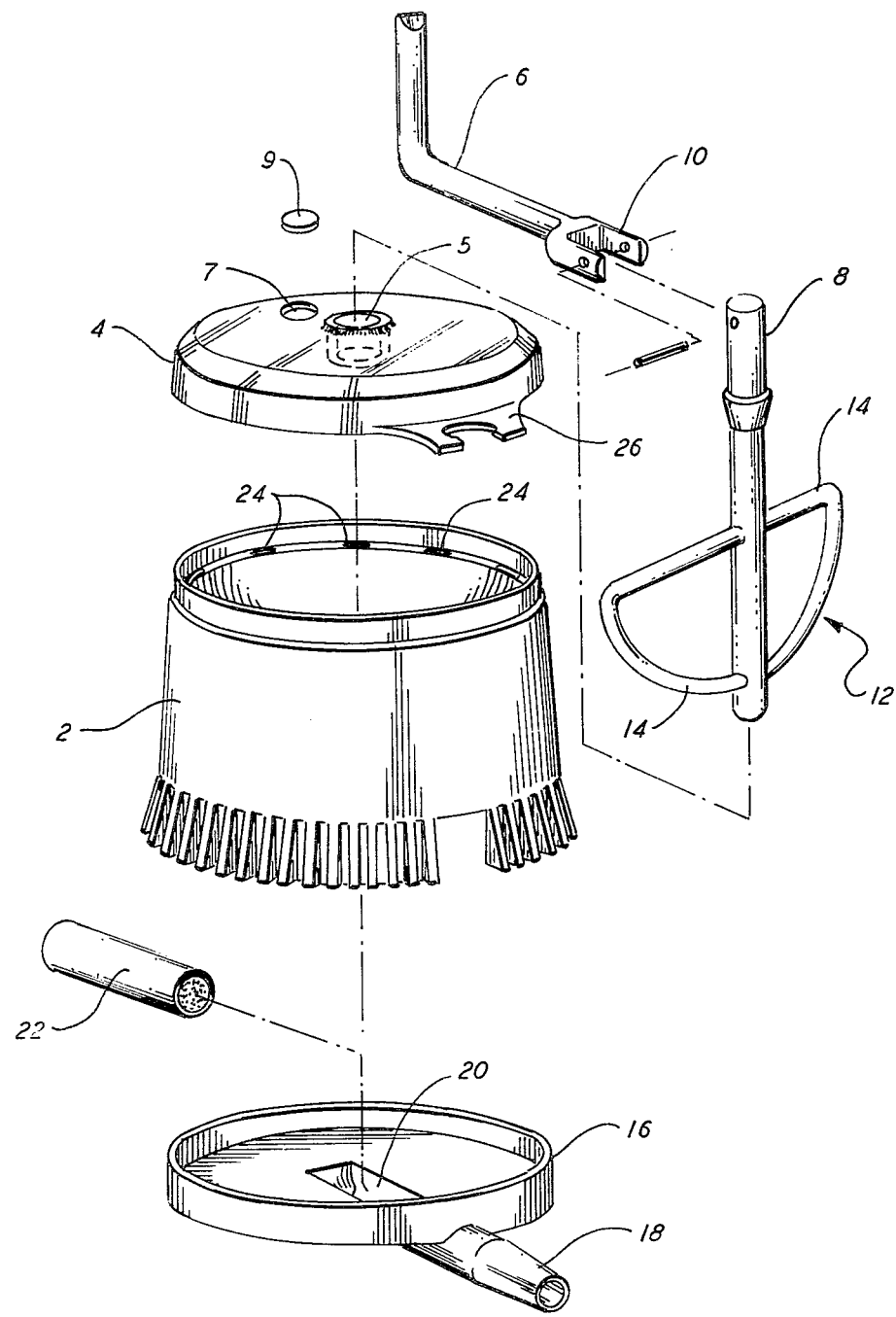
FIG. 3 is a plan view in exploded relationship of the device of FIG. 1.

Referring now to FIG. 3 there is shown a mixing apparatus comprising a reaction-mixing vessel within a housing 2. The open top of the vessel is closeable by means of removable top 4, which is provided with a centrally positioned shaftway 5, and an air vent 7. The air vent is optional and need not be provided if the lid 4 is loosely placed on the housing. Other suitable air venting means to avoid development of excessive vacuum within the apparatus are compatible with the invention. If used, the vent 7 can be fitted with a porous plug 9, which acts as an air filter to prevent solid contaminants, such as dust, from entering the reaction chamber. The bottom of the housing is closed by means of a lower closure 16, which is constructed with an exhaust port 18, designed to protrude through a suitable opening in the housing, and a filter receptacle 20, into which a fume filter shown at 22 can be placed, if desired.

The lid 4 is provided with a rotatable shaft 8 which passes through the lid via the shaftway 5. The shaft is fitted with a foldable handle 6 secured to the upper end of the shaft by means of a yoke 10 and pin 11. The lower end of the shaft 8 which extends into the reaction vessel is fitted with mixing means shown as open paddle 12 comprising a plurality of mixing vanes 14. In order to produce optimum mixing at least one vane passes through the mixture in close proximity to the vessel wall while at least one other, not shown, passes through a circle some distance from the wall in order to agitate the central portion of the reaction mass.

The upper rim of housing 2, as shown, is provided with a plurality of internal fume exhaust vents located around the inside of the rim of the housing 2. These are shown at Nos. 24. These vents communicate through the internal structure of the housing with fume exhaust port 18. Fume exhaust 18 is adapted to be connected to a vacuum source which in operation withdraws gaseous reaction products from the interior of the reaction mixing vessel through the housing and exhaust port 18, into the vacuum system for remote disposal.

Figure 5:
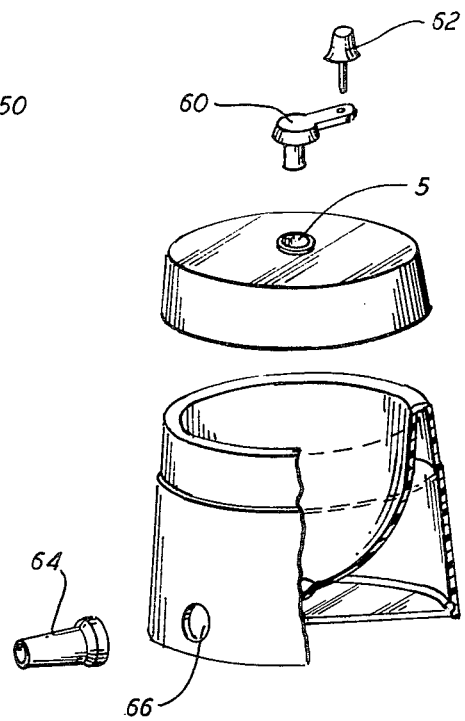
FIG. 5 is an exploded plan view partially in section of another embodiment of the invention.

In FIG. 5 there is shown another embodiment of the invention in which the foldable handle is replaced by a crank 60 which can be the upper end of the shaft. Rotation of the crank causes the shaft and the mixing vanes to rotate and agitate the reaction mixture.

The mixing means is a particularly important element of the apparatus of this invention. Since chemical homogeneity of the bone cement is important to the success of the surgical procedure, it follows that the apparatus must be capable of adequately admixing the reactants, one of which is usually a volatile liquid and the other a fine-powder which often tends to float on the surface of the liquid. The preferred form of mixing means or vane 12 is shown in FIGS. 10, 11 and 12 as comprising shaft 8, a transverse rib 36, and depending ribs 30 and 32 which meet at the base of the vane forming a small bearing 34, which rests on the bottom of the reaction chamber, preferably in a small socket as shown in FIG. 2. The placement of the bearing in a socket tends to stabilize the rotation of the vane through the reaction mass as polymerization progresses. Upper rib 36 is constructed with a flat blade-like structure shown at 38 which acts as a plow to direct powder from the liquid surface into the body of liquid. As shown, both sides of the mixing vane are provided with the mixing plow 38. In practice suitable mixing has been achieved with such a plow on only one side of the vane.

Figure 4:
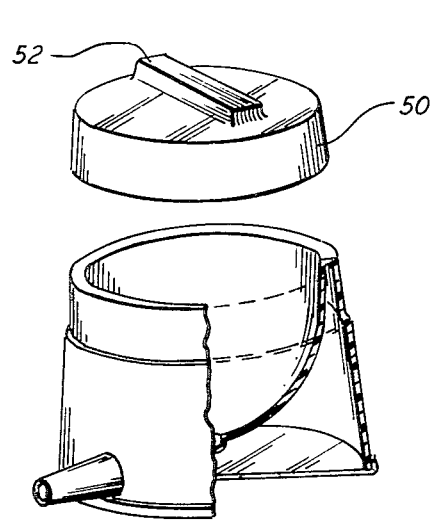
FIG. 4 is a plan view, partially in section of another structural embodiment of the invention.
Figure 6:
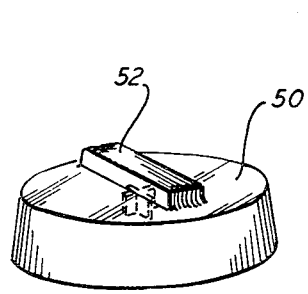
FIGS. 6 and 7 are plan views of alternate covers constituting elements of the invention.
Figure 7:
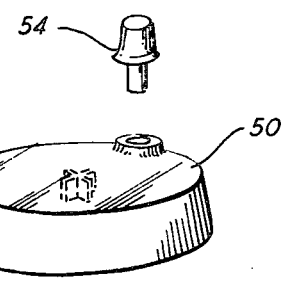

FIGS. 4, 5, 6, 7 and 8 show various structural modifications of the reaction-mixing apparatus of this invention. In FIGS. 4 and 6 rotation of the mixing vane is achieved by rotation of the lid or top 50 by means of hand grip 52. The shaft is integrally molded as part of the top. In FIG. 7 rotation is provided by gripping a small knob shown at 54 located at the outer edge of the circular top 50. The shaft is again integral with the top so that rotation of the top rotates the shaft and mixing means.

Figure 1:
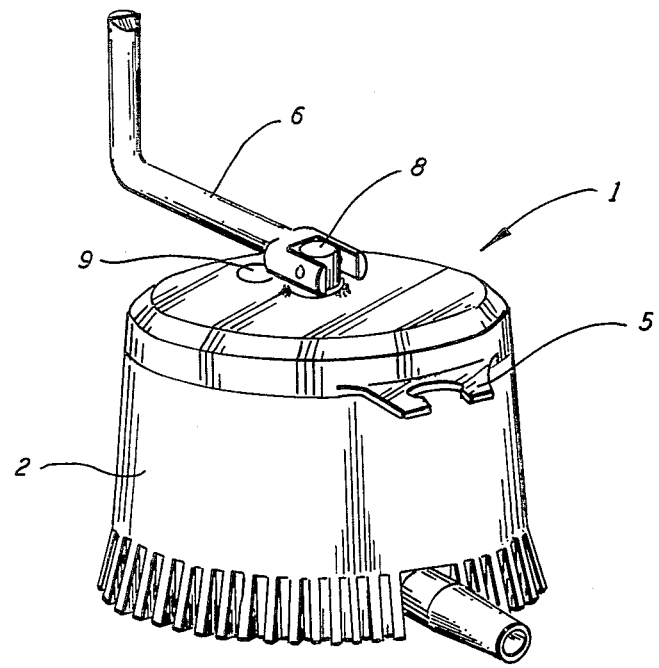
FIG. 1 is a perspective view of a device constituting one embodiment of the invention.

FIG. 5 shows a variation of the foldable handle of FIG. 1. In this embodiment, the shaft passes through the shaftway 5 in top 4 and is joined for rotation to crank 60. The crank is operated by means of knob 62 which functions as a crank handle.

Figure 8:
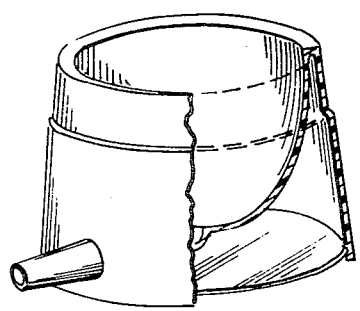
FIG. 8 is a plan view, partially in section of a reaction-vessel which can be used with the covers shown in FIGS. 6 and 7.

The vacuum exhaust port shown in FIG. 1 as element 18 can be molded as an integral part of the housing or it can be separately molded as part of the bottom closure as in FIG. 3. Alternatively, the vacuum port can be a separate piece 64, adapted to plug into an orifice 66, in the side wall of the housing as shown at FIG. 5. If it is desired to provide for filtration or absorption of the exhaust gases, the exhaust port can be provided with a body of charcoal or other absorptive media through which the exhausted fumes are passed prior to entering the vacuum source. The filter media can be located within or without the housing of the mixing apparatus. For example, in FIG. 3 the filter unit 20 is designed to receive a cylindrical filter cartridge 22 having a permeable casing through which all gas withdrawn through port 18 must pass. An alternative construction is shown in FIG. 9 wherein the bottom closure 90 is provided with a pair of upright spaced apart walls 92 and 94 and retaining grooves 96 at the opposite ends thereof. The grooves are designed to receive porous plugs 98 and 100, which act as gas permiable end closures for the filter container 102. One end of the filter unit is positioned against the orifice in the apparatus housing which communicates with the vacuum exhaust port and the top of the unit can be sealed by cover 104, or other suitable means such as a piece of adhesive tape. In operation the fumes flow from the reaction-mixing chamber through the vents and into the housing, thence downwardly to the filter unit which they enter through plug 98. The fumes are drawn through the filter media out through plug 100, and the associated vacuum port. The bottom closure with its associated filter unit can be conveniently secured to the housing by any convenient means of a bead and groove arrangement illustrated in FIG. 5 or by being fitted into a retaining groove in the housing wall as illustrated in FIG. 8. Another alternative for securing the bottom closure to the housing is to employ a bottom having an upwardly extending rim on the outer edge of the bottom piece which mates with and can be sealed to the lower edge of the housing wall.

In operation, the cement components are introduced into the mixing-reaction chamber and admixed by means of the rotating mixing vanes. The gaseous reaction products are withdrawn from the reaction chamber through the filter and vacuum port. The route of gas flow is shown by arrow-shaped indicators in FIG. 2.

What is claimed:

1. A combination mixing-reaction apparatus for admixing reactants which produce gaseous reaction products and removing said reaction products from the apparatus, comprising:
   (a) a housing having upwardly extending walls, a closed bottom and an open top and an exhaust port in said wall adapted for connection to exhaust means;
   (b) a mixing vessel of bowl shaped configuration carried upon and supported by the upper portion of the wall of said housing extending downwardly into said housing defining a space between the walls of the housing and the mixing vessel;
   (c) a removable top cooperating with the housing to close the mixing vessel, thereby containing gaseous reaction products within said vessel;
   (d) at least one vent in the upper wall of said vessel communicating with the interior of the mixing vessel, the space between said vessel and housing and the exhaust port in the wall of said housing;
   (e) mixing means operatively associated with said top extending into the vessel, said mixing means comprising a plurality of open-center mixing vanes, at least one of which extends substantially to the wall of said vessel, and means for rotating said vanes within said vessel.

2. The apparatus of claim 1 having a substantially flat plow member on the upper portion of the vane which extends substantially to the wall of said vessel and the mixing means comprises a rotatable shaft journaled to the removable top.

3. The apparatus of claim 1 wherein the mixing means comprises a shaft integral with the removable top so that rotation of the removable top rotates the shaft and associated vanes.

* * * * *